US00PP21831P3

(12) United States Plant Patent
Hanna et al.

(10) Patent No.: US PP21,831 P3
(45) Date of Patent: Mar. 29, 2011

(54) *PENNISETUM* PLANT NAMED 'TIFTON 23-O'

(50) Latin Name: ***Pennisetum purpureum*×*Pennisetum glaucum***
Varietal Denomination: Tifton 23-O

(75) Inventors: Wayne William Hanna, Chula, GA (US); S. Kristine Braman, Griffin, GA (US)

(73) Assignee: University of Georgia Research Foundation, Athens, GA (US)

( * ) Notice: Subject to any disclaimer, the term of this patent is extended or adjusted under 35 U.S.C. 154(b) by 0 days.

(21) Appl. No.: 12/378,553

(22) Filed: Feb. 17, 2009

(65) Prior Publication Data

US 2010/0212054 P1 Aug. 19, 2010

(51) Int. Cl.
*A01H 5/00* (2006.01)

(52) U.S. Cl. ..... Plt./384

(58) Field of Classification Search ..... Plt./384
See application file for complete search history.

(56) References Cited

U.S. PATENT DOCUMENTS

PP17,728 P3 5/2007 Hanna et al.

OTHER PUBLICATIONS

Ingham et al. Origin of the main class of repetitive DNA within selected *Pennisetum* specieds. Mol. Gen. Genet. (1993) 238: 350-356.*

Hanna, Wayne, William, U.S. Appl. No. 12/378,547, filed Feb. 17, 2009, *Pennisetum* 'TIFT-17', 9 pages.

* cited by examiner

*Primary Examiner*—June Hwu
(74) *Attorney, Agent, or Firm*—Davis Wright Tremaine LLP

(57) ABSTRACT

The new variety *Pennisetum* 'Tifton 23-O' is provided. The new and distinct variety has increased tillers under drought conditions; superior *Helminthosporium* leaf spot resistance; high ornamental value; narrow canopy; narrow base; and narrow leaves. The asexually reproduced inter-specific variety is reliably propagated vegetatively.

1 Drawing Sheet

Latin name of the genus and species of the plant claimed: 'Tifton 23-O' is an inter-specific ornamental *Pennisetum* hybrid of the genus and species *Pennisetum purpureum*× *Pennisetum glaucum.*

Variety denomination: The new *Pennisetum* claimed is of the variety denominated 'Tifton 23-O'.

BACKGROUND OF THE INVENTION

The present invention relates to a new and distinct cultivar of *Pennisetum* botanically known as *Pennisetum purpureum*× *Pennisetum glaucum,* and herein referred to as 'Tifton 23-O'.

The new *Pennisetum* is a product of a planned breeding program conducted by the Inventors in Tifton, Ga. The objective of the *Pennisetum* breeding program is to create new plant cultivars with improved commercial qualities. This cultivar is commercially important for its superior ornamental value, since the plant (crown and base) and the leaves are narrower, giving it a fine-textured appearance. Moreover, it shows better pest resistance. These and other qualities are enumerated herein.

Pedigree and history: In 2003, napiergrass (unpatented, *Pennisetum purpureum,* 2n=4x=28, designated 'N240-8', the female parent) was crossed with red pearl millet (unpatented *Pennisetum glaucum,* the male parent). The new variety 'Tifton 23-O' was selected in 2004 from the 2003 cross.

Asexual reproduction of the new *Pennisetum* by vegetative propagation (single stem propagules) in a controlled environment in Tifton, Blairsville and Griffin, Ga. since 2005, has shown that the unique features of this new *Pennisetum* are stable and reproduced true to type in successive generations.

SUMMARY OF THE INVENTION

The new variety *Pennisetum* 'Tifton 23-O' has not been observed under all possible environmental conditions. The phenotype may vary somewhat with variations in environment and cultural practices such as temperature and light intensity without, however, any variance in genotype.

The following traits have been repeatedly observed in Tifton, Blairsville, and Griffin Ga., and are determined to be the unique characteristics of the new variety 'Tifton 23-O':

1. Superior tiller numbers under drought conditions;
2. Superior *Helminthosporium* leaf spot resistance;
3. High ornamental value;
4. Narrow canopy;
5. Narrow base;
6. Narrow leaves.

The new variety *Pennisetum* 'Tifton 23-O' can be compared to its parents, as well as other grasses developed by University of Georgia researchers, such as the patented (U.S. Plant Pat. No. 18,509) *Pennisetum* 'Prince', patented (U.S. Plant Pat. No. 17,728) *Pennisetum* 'Princess', and co-pending plant patent application for 'Tift-17' (U.S. Plant patent application Ser. No. 12/378,547), filed on the same date as the instant application.

Comparison to 'N240-8'. The new variety 'Tifton 23-O' is similar to 'N240-8' in the absence of trichomes on both leaf surfaces, sheath, and leaf blade margin trichomes. Both are perennials and neither flower in late October in Tifton, Ga. The new variety 'Tifton 23-O' is shorter and has different leaf color (adaxial surface, abaxial surface and midrib) than 'N240-8'. The new variety 'Tifton 23-O' has shorter leaf length and narrower leaf width than 'N240-8'. The new variety 'Tifton 23-O' has slightly shorter trichomes on the leaf collar than 'N240-8'. The new variety 'Tifton 23-O' has approximately 2 mm long trichomes about 3 cm from collar on the leaf blade edge whereas 'N240-8' has slightly longer leaf blade edge trichomes, slightly farther from the collar. The new variety 'Tifton 23-O' is not disease-susceptible to *Helminthosporium* leaf spot, whereas 'N240-8' is susceptible to this disease.

Comparison to red tetraploid millet. The new variety 'Tifton 23-O' has similar abaxial leaf and midrib color to red millet. Neither the new variety 'Tifton 23-O' nor red millet has adaxial or abaxial leaf surface, or sheath trichomes. The new variety 'Tifton 23-O' is approximately 50% shorter than red millet. The new variety 'Tifton 23-O' has shorter leaf length and narrower leaf width than red millet. The new variety 'Tifton 23-O' has inconspicuous leaf blade margin trichomes, whereas red millet has slightly apparent leaf blade margin trichomes. The new variety 'Tifton 23-O' has less dense and shorter leaf collar trichomes than red millet. The new variety 'Tifton 23-O' has approximately 2 mm long trichomes about 3 cm from collar on the leaf blade edge whereas red millet has none. The new variety 'Tifton 23-O' is a perennial at Tifton, Ga., whereas red millet is an annual at the same location. The new variety 'Tifton 23-O' is not disease-susceptible to *Piricularia grisea* leaf spot, whereas red millet is susceptible to this disease. The new variety 'Tifton 23-O' has no inflorescences in late October, in Tifton, Ga., whereas red millet does have inflorescences.

Comparison to 'Prince'. The new variety 'Tifton 23-O' is significantly shorter than 'Prince'. It was significantly shorter than 'Prince' in 5 of 6 tests. Leaf length of the new variety 'Tifton 23-O' is significantly shorter than that of 'Prince'. The new variety 'Tifton 23-O' rated a significantly higher ornamental value than 'Prince' in all tests and in two of three tests for color. Field trials indicate that the new variety 'Tifton 23-O' has improved resistance to *Helminthosporium* leaf spot as compared to 'Prince'.

Comparison to 'Princess'. The new variety 'Tifton 23-O' was significantly shorter than 'Princess' in four of seven tests. Canopy and plant base of the new variety 'Tifton 23-O' tended to be narrower or similar to that of 'Princess'. Leaves of the new variety 'Tifton 23-O' were narrower in three of four tests and similar in length to that of 'Princess'. The number of tillers were similar for the new variety 'Tifton 23-O' and 'Princess' except under drought stress conditions, when the new variety 'Tifton 23-O' produced significantly more tillers. The new variety 'Tifton 23-O' rated significantly better than 'Princess' for ornamental value at 2 of 3 locations and in 1 of 2 years for color. The new variety 'Tifton 23-O' showed better resistance to *Helminthosporium* leaf spot than 'Princess' in two of three tests.

Comparison to co-pending 'Tift-17'. 'Tift-17' is approximately twice as tall, has longer and wider leaves, has unmottled leaves, has longer trichomes on the leaf blade edge at the collar, with those trichomes placed further away from the collar, and has sheath trichomes whereas the new variety 'Tifton 23-O' does not. 'Tift-17' is otherwise similar to the new variety 'Tifton 23-O' in that it has similar abaxial leaf color, midrib color, has no trichomes on either leaf surface, is cold tolerant and disease resistant, and does not flower in late October.

BRIEF DESCRIPTION OF THE FIGURES

The accompanying photographic illustration shows typical specimens in full colour of the foliage of the new variety *Pennisetum* 'Tifton 23-O'. The colors are as nearly true as is reasonably possible in a color representation of this type.

BOTANICAL DESCRIPTION

Figure 1:
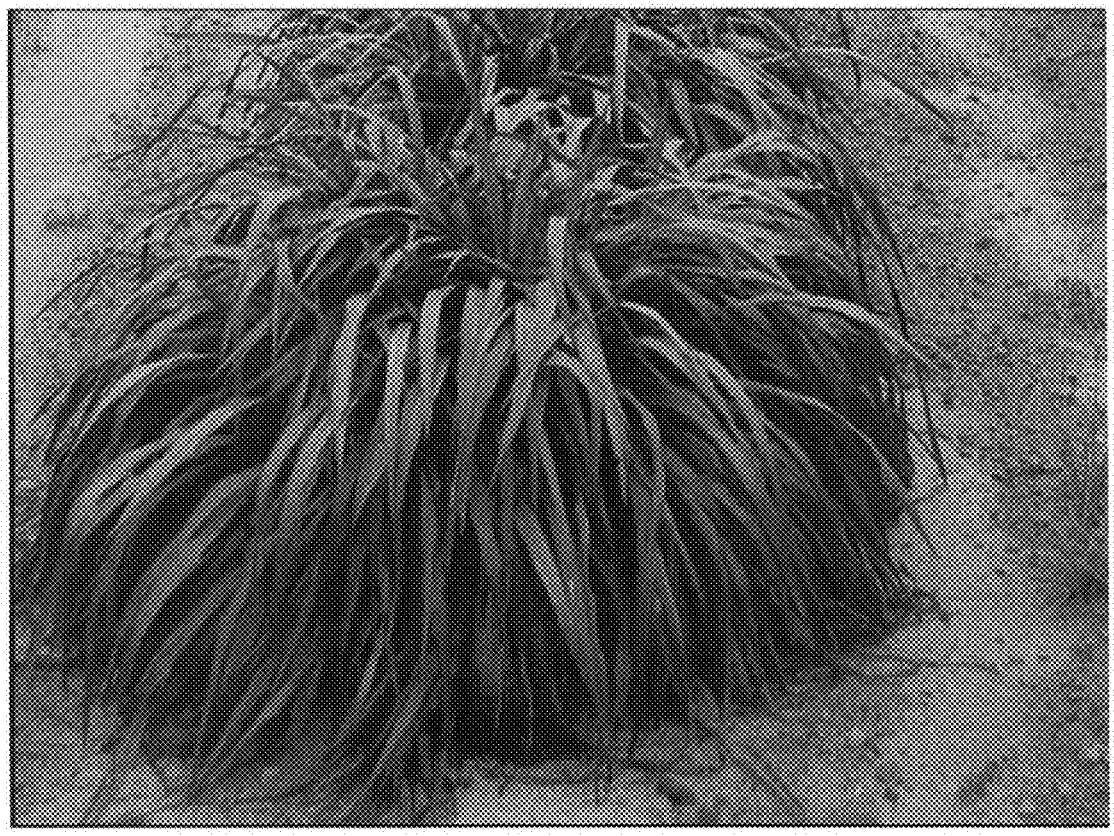
FIG. 1 is a photograph of the new variety *Pennisetum* 'Tifton 23-O'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following observations, measurements and values describe plants grown in Tifton, Blairsville, or Griffin, Ga. During the growing of the plants, day temperatures ranges from approximately 50° F. to approximately 99° F. and night temperatures ranges from approximately 20° F. to approximately 70° F.

The new variety 'Tifton 23-O' is a weak perennial at Tifton, Ga. (U.S.D.A. zone 8a). The new variety 'Tifton 23-O' is pollen and seed sterile and does not produce seed heads at Tifton, Ga. in the field.

All data are from plants established as single stem propagules in mid-May, and rated in September through October. Plants were spaced at 2 meter centers. Color indicators are according to The Royal Horticultural Society (R.H.S.) Colour Chart, 5$^{th}$ Edition.

Other data are as follows:

*Mature plant height.*—Approximately 53-77 cm.

*Culm.*—Approximately 40 cm long for plants that are 150 days old; completely covered by leaf sheath.

*Diameter of plant canopy.*—Approximately 67-147 cm.

*Diameter of base.*—Approximately 21-35 cm.

*Leaf width.*—Approximately 18-22 mm.

*Leaf length.*—Approximately 46-67 mm.

*Leaf apex shape.*—Apiculate, ending in a sharp point.

*Adaxial leaf surface trichomes.*—None.

*Abaxial leaf surface trichomes.*—None.

*Leaf blade margin trichome length.*—Inconspicuous.

*Leaf collar trichome length.*—Approximately 1 mm.

*Leaf blade edge at collar trichome.*—Approximately 2 mm long for about 3 mm from collar.

*Ligule.*—No membranous ligule present; lined with trichomes.

*Sheath trichomes.*—None.

*Number of tillers.*—Approximately 34-119.

*Adaxial leaf color.*—About mottled Greyed-purple RHS 187D/137B.

*Abaxial leaf color.*—About Greyed-purple RHS 187B.

*Midrib color.*—About Greyed-purple RHS187B.

*Inflorescence.*—None.

What is claimed is:

1. A new and distinct variety of the *Pennisetum* plant named 'Tifton 23-O', substantially as illustrated and described herein.

* * * * *